United States Patent
Olsson et al.

(10) Patent No.: US 6,442,289 B1
(45) Date of Patent: Aug. 27, 2002

(54) EXTENDED FIELD OF VIEW ULTRASONIC DIAGNOSTIC IMAGING

(75) Inventors: Lars Jonas Olsson, Woodinville; Roy B. Peterson, Seattle; Thomas Martin Wissler, Kenmore, all of WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/345,244

(22) Filed: Jun. 30, 1999

(51) Int. Cl.[7] .................................................. G06K 9/00
(52) U.S. Cl. ........................ 382/128; 73/1.82; 600/437
(58) Field of Search ................................ 382/100, 128, 382/294, 130, 190, 218, 236, 260, 261–266, 278–279, 299; 348/169; 600/443, 459, 463, 441; 378/62; 73/1.82, 1.86

(56) References Cited

U.S. PATENT DOCUMENTS

| | | | |
|---|---|---|---|
| 5,538,004 A | 7/1996 | Bamber | 600/443 |
| 5,566,674 A | 10/1996 | Weng | 600/443 |
| 5,575,286 A | 11/1996 | Weng et al. | 600/444 |
| 5,655,535 A | 8/1997 | Friemel et al. | 600/443 |
| 6,014,473 A | 1/2000 | Hossack et al. | 382/294 |
| 6,059,727 A * | 5/2000 | Fowlkes et al. | 600/443 |
| 6,126,599 A * | 10/2000 | Jago et al. | 600/437 |
| 6,159,152 A | 12/2000 | Sumanaweera et al. | 600/443 |
| 6,311,540 B1 * | 11/2001 | Paltieli et al. | 73/1.82 |

FOREIGN PATENT DOCUMENTS

| | | |
|---|---|---|
| DE | 196 11 990 | 10/1996 |
| WO | WO 00 24316 | 5/2000 |

OTHER PUBLICATIONS

Rohling et al., "Three–demensional spatial compounding of ultrasound images," Medical Image Analysis (1996/7) vol. 1, No. 3, pp. 177–193, Oxford University Press.

Moskalik et al., "Registration of Three–dimensional Compound Ultrasound Scans of the Breast for Refraction and Motion Correction, " Ultrasound in Med. & Biol. vol. 21, No. 6, pp. 769–778, 1995.

Rohling et al., "Automatic Registration of 3–D Ultrasound Images," Ultrasound in Med. & Biol., vol. 24, No. 6, pp. 841–854, 1998.

* cited by examiner

Primary Examiner—Jayanti K. Patel
(74) Attorney, Agent, or Firm—W. Brinton Yorks, Jr.

(57) ABSTRACT

An extended field of view image is formed by combining a plurality of spatially offset ultrasonic images which have been spatially aligned. Images which are to be aligned are processed to produce two sets of corresponding images of progressively lower resolution. The spatial alignment is performed by comparing images of the same resolution level from each set, and progressing from comparison of the lowest resolution images to comparison of the highest. Only prominent feature areas of the images are used in the comparison to improve alignment reliability and to reduce computational needs. As each pair of images is compared, the result of the comparison is used to pre-align the images of the next resolution level. Results are checked and refined against boundary conditions and by gradient refinement.

7 Claims, 7 Drawing Sheets

EXTENDED FIELD OF VIEW ULTRASONIC DIAGNOSTIC IMAGING

This invention relates to ultrasonic diagnostic imaging systems and, in particular, to ultrasonic diagnostic imaging systems which produce ultrasonic images with an extended field of view.

Ultrasonic diagnostic imaging systems of the 1970s and 1980s were manufactured with what is known as B-arm scanning. In B-arm scanning systems an A line (single beam) transducer was mounted at the end of an articulated arm. The joints of the articulated arm contained sensors which continuously monitored the relative positions of the arm segments, enabling the spatial position of the transducer to be constantly tracked. As the transducer was scanned over the body of the patient, the relative spatial locations of consecutive A lines was computed from the articulated arm sensors, and the A lines were assembled in consecutive, side-by-side locations on an image display. The B arm system was thus capable of painting an ultrasonic image that could laterally extend for the maximum number of successive A lines that the system could store and display and over which the B arm could extend.

In recent years electronically scanned array transducers have been adapted for the same purpose. Since an electronically scanned array transducer automatically produces a two dimensional image, movement of the array transducer in the plane of the image will produce successive, spatially offset two dimensional images. Each new image in a new spatial location can be spatially registered with a previously acquired image with which it overlaps, then combined with the previous images to produce an extended image which is laterally extensive in the direction of motion of the array transducer. The extent of the extended field of view image is determined by the capacity of the ultrasound system to store and display multiple partially overlapping two dimensional images.

An important feature of such extended field of view (EFOV) imaging systems is the ability to quickly and simply register a newly acquired image with the previously assembled extended images. Many techniques are available for registering images by estimating the displacement of one image to another, including cross correlation searching, block matching algorithms, aligning for maximum brightness and others. The algorithms employed by these techniques may be first order, global transformations (translation and/or rotation) or higher order complex processes, based on the nature and magnitude of the displacements. But most of these techniques are highly computationally intensive, requiring extensive processing of a large amount of pixel data. Accordingly it would be desirable to utilize an efficient and reliable technique to register successive images for the production of an extended field of view ultrasonic display.

In accordance with the principles of the present invention, an extended field of view ultrasonic diagnostic imaging system is provided in which images are registered on the basis of significant features of the images. The matching of significant features of two images has been found to reliably and rapidly produce the displacement measures necessary to align the images. In a preferred embodiment each image is initially processed to produce a set of images of different levels of resolution, each highlighting image features of different levels of significance. Image pairs of corresponding resolution are then processed to measure the spatial displacement between the images, with images of different levels of resolution yielding measures which can be related to produce a highly refined displacement measure.

Figure 1:
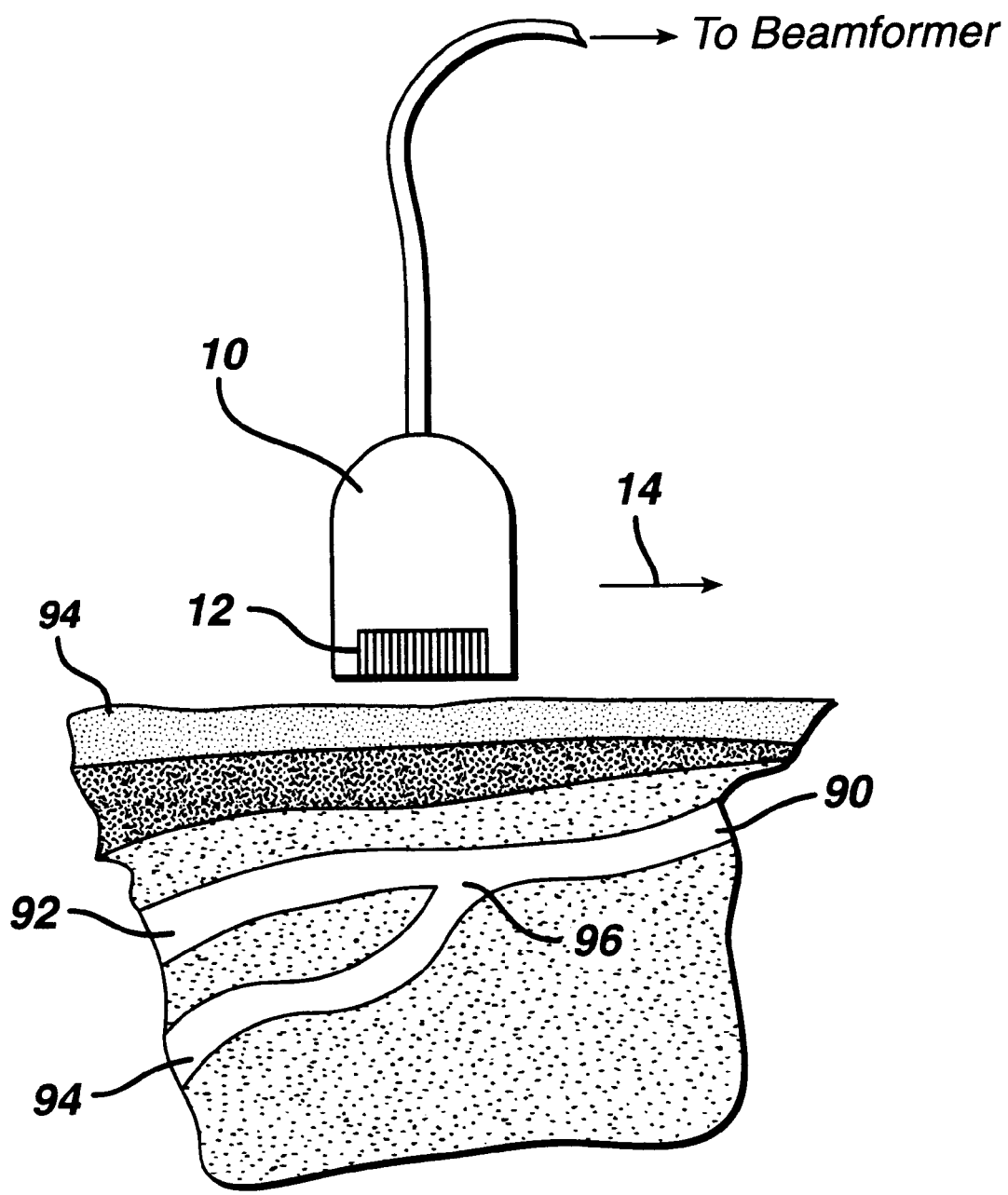
FIG. 1 illustrates the technique for scanning an array transducer to produce an extended field of view image.

Referring first to FIG. 1, the technique for scanning an array transducer to produce an extended field of view image is shown. An ultrasonic scanhead 10 which includes an electronically scanned array transducer 12 is shown in contact with the skinline 94 of a patient. In this example the clinician wants to scan a length of blood vessels 90,92,94, and to display the blood vessels in an extended field of view image. As the drawing shows, only the narrow region of the bifurcation 96 is directly beneath the aperture of the array transducer 12 and hence viewable in a single conventional image. To scan a length of the blood vessels, the clinician slides the scanhead in the direction 14, which denotes a direction co-aligned with the longitudinal axis of the array transducer and the plane of an image. As the scanhead is moved in the direction 14, successive planar images referred to herein as elemental images are acquired, each being slightly displaced (as a function of the speed of scanhead motion and the image acquisition rate) in the direction 14 from the previous image. The displacement between successive elemental images is computed and the images are registered and combined on the basis of the displacements to produce a composite extended field of view image of the blood vessels.

Ideally, it is desirable for the scanhead to be translated at a constant speed while images are acquired, so that individual elemental images are not stretched or compressed laterally relative to earlier acquired elemental images. It is also desirable for the scanhead to be moved in a single plane, so that there is high correlation from each elemental image to the next. However, manual scanning over an irregular body surface often causes departures from either or both of these desirable conditions. As will be seen below, the present invention provides solutions to the effects of less than desirable manual scanning.

Figure 2:
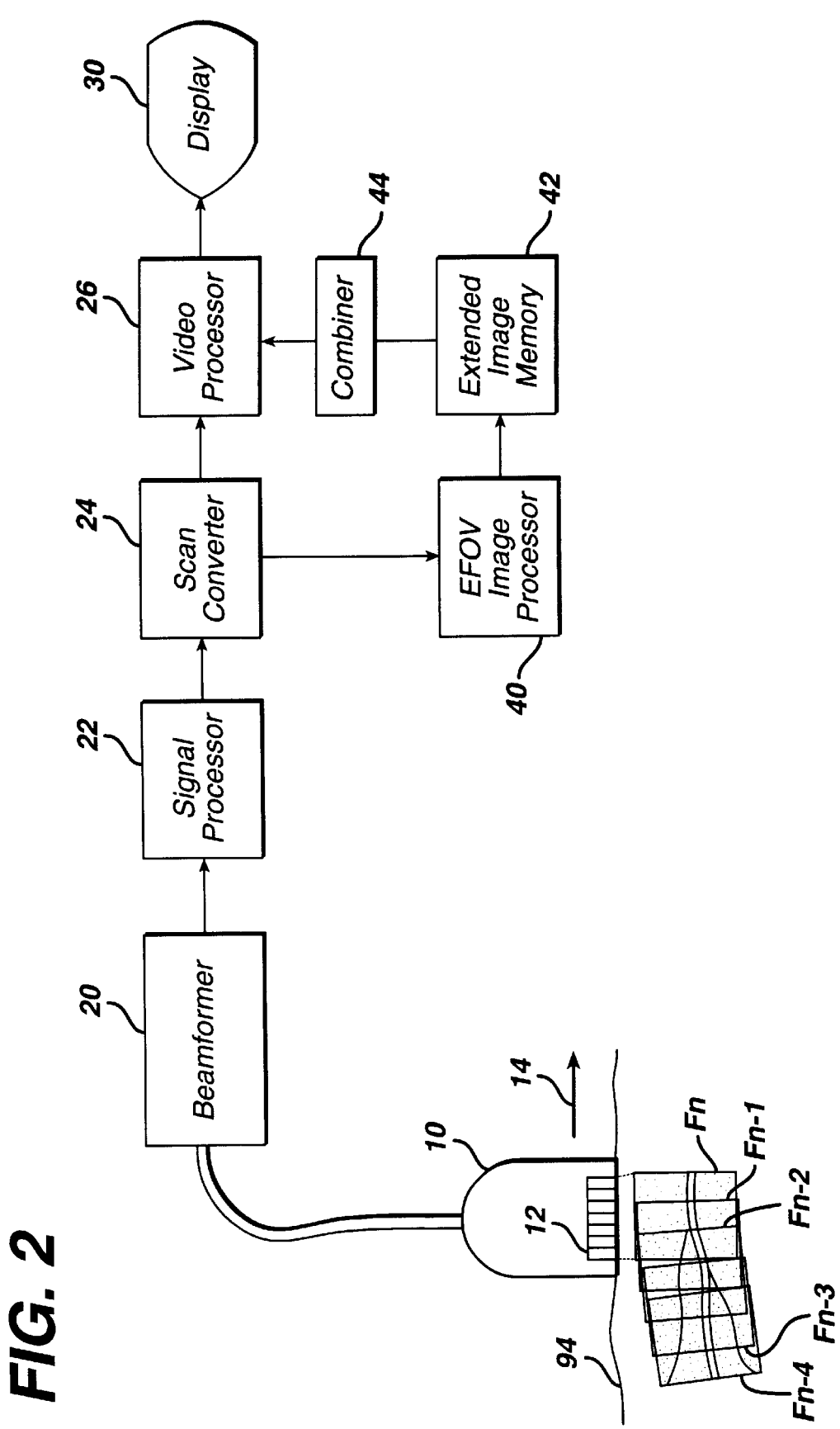
FIG. 2 illustrates an extended field of view ultrasonic diagnostic imaging system constructed in accordance with the principles of the present invention.

An ultrasonic diagnostic imaging system for producing extended field of view images in accordance with the principles of the present invention is shown in FIG. 2. The scanhead 10 is moving in the direction 14 of the planes of successively acquired images $F_{n-4}$–$F_n$. The acquired images $F_{n-4}$–$F_n$ are transparently shown in this drawing so that their spatial overlap can be appreciated. The first image acquired in this sequence is image frame $F_{n-4}$, and the last image acquired is frame $F_n$, shown in alignment with the aperture of the array transducer 12. The echoes of each acquired image frame are formed into beams by beamformer 20. The coherent echoes are then processed by a signal processor 22 and arranged in respective ultrasonic images by a scan converter 24. To form conventional real time images, each image is coupled to a video processor 26 and displayed on an image display 30.

In accordance with the principles of the present invention, each image is coupled to an EFOV image processor 40. The EFOV image processor, which may operate with either estimate data (pre-scan converted) images or display data (scan converted pixel data) images, receives each newly acquired image during the EFOV mode of operation and computes the displacement between the new image and the previously acquired elemental image of the EFOV image, as more fully described below. The EFOV image processor stores the new image in registration with the previously acquired elemental images in an extended image memory 42 as described below. Each time the EFOV image is extended by the addition of new image data, the EFOV image data stored in the extended image memory 42 is extracted from the memory and combined by a combiner 44 to form a new EFOV image, which is coupled to the video processor 26 for viewing on the display.

FIGS. 3a–3d illustrate a preferred technique in accordance with the present invention for computing the displacement between images so that multiple offset elemental images may be registered and combined into a single EFOV image. The two images which are to be registered can be the newly acquired elemental image and the previously formed EFOV image. In the preferred embodiment of the present invention the newly acquired elemental image is registered with the previously acquired elemental image. The first step is to process each image into a set of images of different levels of resolution. The starting images have the highest resolution in the set, and each additional image in the set exhibits progressively coarser resolution. A set of four such images is shown in FIGS. 3a–3d, with image 32 being the received elemental image, and each of the other images 34, 36, and 38 having progressively coarser resolution. Images 34, 36, and 38 can be produced by a variety of methods. Images 34, 36 and 38 can be produced by passing image 32 through low pass filters of progressively lower cutoff frequencies. Images 34, 36 and 38 can be produced by successive downsampling and/or truncating of the image data of image 32. As FIGS. 3a–3d show, each image of progressively coarser resolution clearly shows only image features of increasing significance in the image. For instance, the highly resolved mitten-shaped structure 50 in image 32 shows less fine detail in the same structure 52 in the lower resolution image 34 of FIG. 3b. Only higher level details of the same structure 54 are seen in the lower resolution image 36 of FIG. 3c, and only the highest level outline 56 of the same structure is seen in the lowest level resolution image 38 of FIG. 3d. One way to segment the levels of resolution is to produce an image 34 with half the resolution of the original image 32, an image 36 with half the resolution of image 34, and an image 38 with half the resolution of image 36.

In the next step in the process, the lowest resolution image 38 from two elemental images are compared with each other to ascertain the spatial displacement between the two. In a preferred embodiment, only a small area around a single point in the image is used for the comparison. The point can be the location of a prominent feature in the image or an arbitrary point such as the center of the image. A suitable area over which to perform the comparison is an eight pixel by eight pixel area 60 around the point indicated by the "+" symbol in FIG. 3d. The areas 60 of the two images are aligned in various ways to determine the alignment in which the coarsely defined feature(s) in the area are most closely in congruence. A systematic way for performing these alignments is to carry out a sum absolute difference (SAD) search of the pixels around the + point in each image to determine the minimum SAD which indicates the best match. The SAD search compares pixels P by performing comparisons in accordance with the algorithm $$\sum_{y=0}^{8}\sum_{x=0}^{8} |P_{n(X-x-dx,Y-y-dy)} - P_{o(X-x,Y-y)}|$$

Where $P_n$ is a pixel of the newly acquired image, $P_o$ is a pixel of a previous (old) image, x and y are the parameters over which the summations are performed, and X and Y are the reference coordinates of the feature in the pixel area, generally at the center of the area. The algorithm is iterated for alignment offsets dx,dy until min SAD(X,Y,dx,dy) is found. As the SAD search is being carried out, boundary conditions are constantly checked to ascertain whether a result is a true minimum or only an aberrational value. For example, a minimum SAD occurring when the center point + of one area is aligned with the edge of the search area would be ignored. Minimum SAD values are also compared against thresholds for validity in terms of both magnitude and percentage values. Each SAD calculation includes a comparison against the condition of no offset, where the displacement parameters are set to zero. Since the images being compared are of the coarsest resolution level, only the most significant features of the image will be present in the data sets, and the process will result in the closest alignment of these significant image features.

Once a min SAD value has been found for the two pixel areas the parameter estimate is refined by a gradient search algorithm. This algorithm computes the differentials of the SAD value as a function of small offsets in each of the displacement parameter dimensions (x,y,θ) used to compute the min SAD. If an offset results in an improved SAD value, the displacement parameters are replaced with the refined offset parameters. The refinement process can be iteratively repeated a number of times, each with an increasingly finer offset.

Figure 3B:
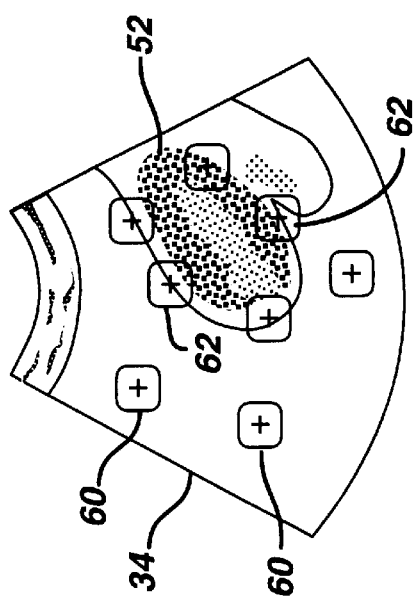
FIGS. 3a–3d illustrate image registration using a set of images exhibiting different levels of resolution.
Figure 3D:
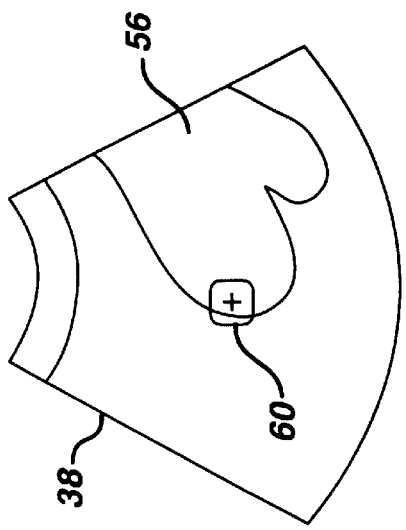
Figure 3A:
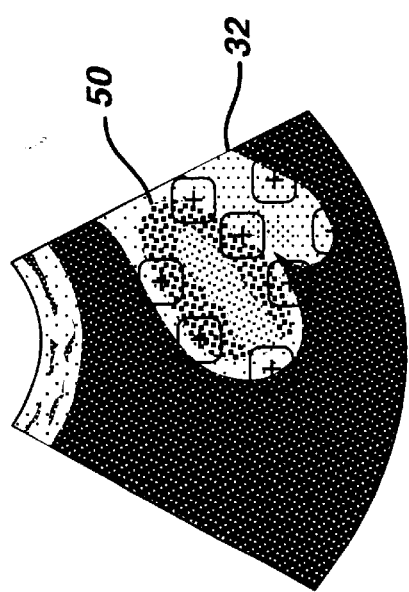
Figure 3C:
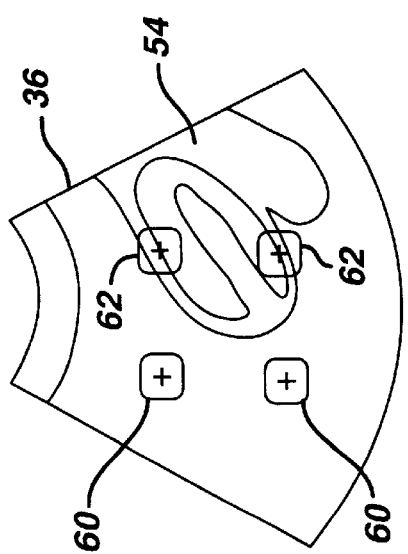

In the next step, the same comparison is made of the old and new images of the next highest level of resolution. This time, the comparison is made using a greater number of small image areas such as those indicated by the small boxes 60,62 in FIG. 3c. The points + around which the areas are located can be chosen arbitrarily but preferably are chosen to include identified image features. In FIG. 3c the location of box 60 is arbitrarily chosen, while box 62 is defined to be located on features of image structure 54. Again a systematic comparison of corresponding pixel areas such as a min SAD search is performed. Preferably, the alignment analysis for the second and subsequent resolution levels begins with the two images initially aligned (pre-warped) as determined by the displacement measure resulting from the analysis of the previous level. Before applying the displacement parameters of the previous level it may be necessary to scale them, as there may be differences in pixel size and/or density from one level to the next due to the resolution difference.

At the second and subsequent resolution levels where multiple small pixel areas 60,62 are analyzed for min SAD, a predetermined number of the areas must yield a valid min SAD value before the previous displacement parameter values will be replaced by new ones. For example, if the comparisons of at least three of the four areas 60,62 of the second resolution level each yield a valid minimum SAD, then the three or four results are aggregated and used as the new displacement parameters. If less than three areas yield a valid min SAD, then the results are discarded and the parameters of the image comparison at the previous resolution level are retained as the preferred displacement parameters. Again, boundary conditions are checked to prevent aberrational results from being used as registration parameter values.

Figure 5B:
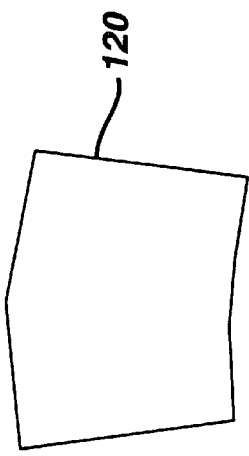
FIGS. 5a and 5b illustrate three overlapping elemental images which form an extended field of view image.

Two more registration analyses of the two higher resolution image sets 34 and 32 are performed in accordance with this same process. Preferably, the analyses at the higher resolution levels are performed with a greater number of pixel areas of comparison. For example up to sixteen areas 60,62 can be used in the comparisons involving images 34 and 32, with each pixel area preferably chosen to correspond with a significant feature in the image. Features are defined as regions of the image that contain structures that can be matched accurately and robustly such as points and corners. If the results of these comparisons yield better parameter values, the new displacement parameters are used. If no better parameters are found, the previous results are retained as the displacement parameters. The gradient refinement process can be applied at these higher resolution levels by using a number of feature areas or arbitrarily chosen points at different image locations, retaining displacement parameters which yield an improved overall min SAD result. These refined parameters are then used to align the new elemental image with the previous elemental image of the EFOV image. The new elemental image is added to the previous images in a history buffer as described below in conjunction with FIGS. 5–7.

Prior art techniques for measuring image displacement are generally computationally intensive. That shown in U.S. Pat. No. 5,566,674, for instance, performs a computation for every pixel area of each entire high resolution image. The technique of the present invention does not require such intensive processing, relying as it does on comparisons of just a few small, discrete areas of each image. Improved accuracy and robustness are provided by the use of multi-resolution levels of the same image which tend to produce fewer local minima, and the use of feature-based comparisons, rather than blindly processing all the data of every image. This is illustrated by the SAD characteristics of FIGS. 4a–4c.

The use of multiple small pixel areas for alignment analysis permits accurate alignment of elastically deformed images. For example, an elemental image may be laterally stretched or compressed relative to the previous elemental image by reason of changes in the speed at which the scanhead is moved during scanning. Image deformation within an image can occur due to motion of the anatomy being scanned, such as the heart. If scanhead motion is increasing, a new image can be stretched in relation to a previous image, and can be relatively compressed if scanhead motion is decreasing. The degree of elasticity is a function of both scanhead motion and the directional sequence in which the scanlines of the image are transmitted. By computing min SAD at a plurality of separate image areas 60,62, separate portions of the old and new images can be separately aligned. Registration parameters for intermediate image regions can be scaled in proportion to the parameters calculated for the specific areas 60,62. Thus, elastic deformation errors can be overcome and eliminated from the registration process.

Figure 4A:
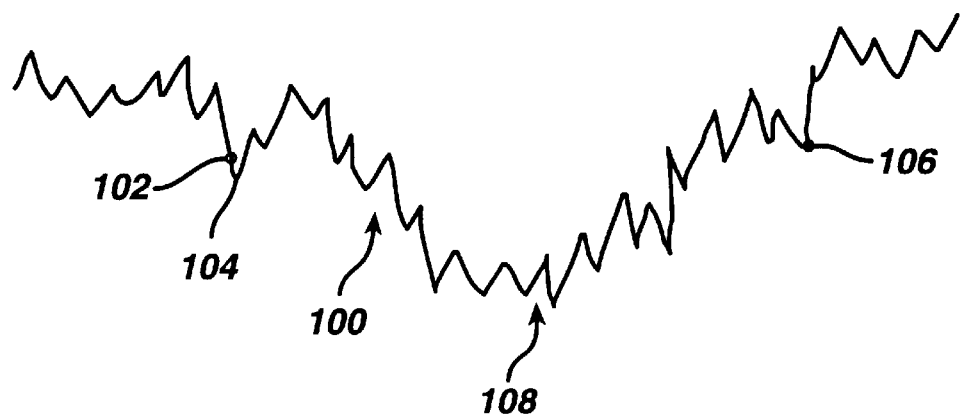
FIGS. 4a–4c illustrate SAD characteristics for images of different levels of resolution.
Figure 4B:
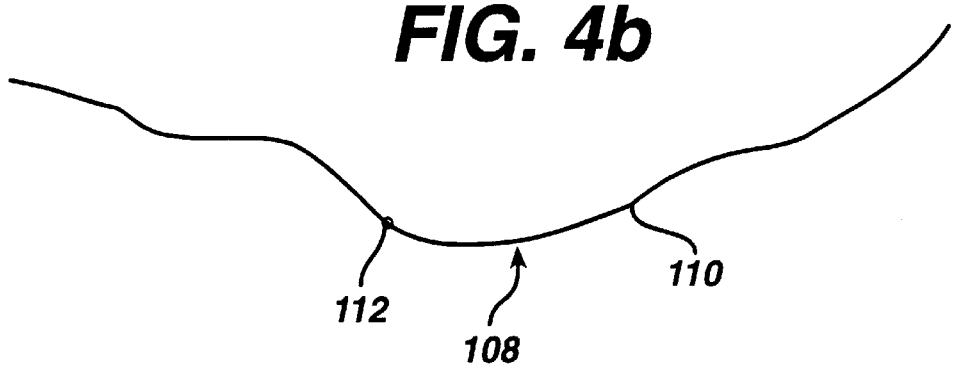

FIG. 4a illustrates a typical SAD characteristic 100 for a full resolution image 32 which might result from the calculation and plotting of a complete SAD characteristic for an alignment parameter. In a constructed embodiment of the present invention only a few points of such a SAD characteristic are computed and compared as the processor 40 tries to locate the minimum SAD point 108. Due to the high spatial frequency content of the high resolution image 32, the SAD characteristic is likely to exhibit points 104,106 of local minima in addition to the overall minimum 108. This can be due to alignment of image artifacts such as speckle, for instance. Thus, the SAD analysis can lead to identification of a point 102 that is approaching a local minimum 104, rather than the overall characteristic minimum 108.

Figure 4C:
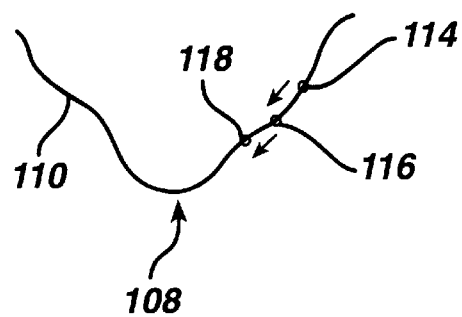

However, the use of different image resolution levels will cause the SAD characteristics of the coarser resolution level images to exhibit far less high spatial frequency content. Accordingly, the SAD characteristics of these lower resolution renditions will appear as shown by SAD characteristic 110 of FIG. 4b, in which the local minima of the high resolution SAD characteristic are smoothed over. Thus, an initial estimate of the minimum SAD point may be located at point 112 and approaching the overall characteristic minimum 108 rather than some local minima. The initial pre-warping, gradient refinement processing, and iterative SAD computations at higher levels of resolution will cause an initial min SAD estimate 114 to iteratively progress to points 116 and 118, as shown in FIG. 4c, to progressively home in on the desired minimum SAD point 108.

Figure 6:
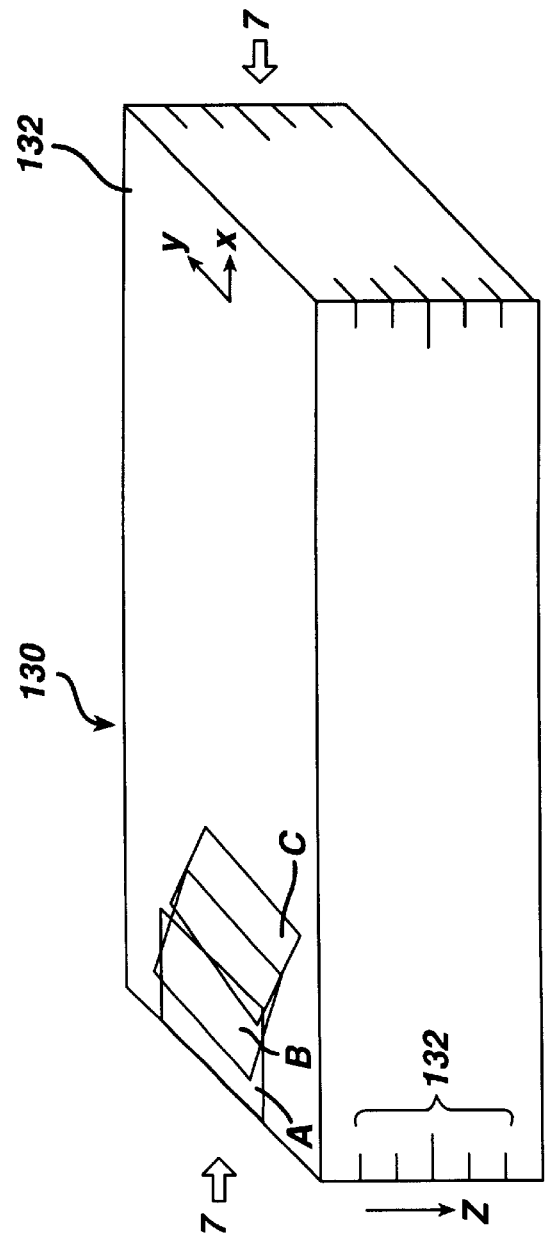
FIG. 6 depicts the organization of an extended field of view history buffer.

When the displacement necessary to align a new elemental image to the previous elemental image in an EFOV series is known, the new elemental image can be combined with the others to produce an extended image. One way to do this is to employ an EFOV image buffer 42 in which a single EFOV image formed from previously acquired elemental images is stored. The new elemental image is then added to the EFOV image in the buffer, generally through some form of weighting or averaging, to produce a new EFOV image for display. Once the new elemental image has been added to the EFOV image it can no longer be separately identified, as it is blended into and becomes an integral part of the EFOV image. In accordance with a further aspect of the present invention, it is preferable to use a history buffer for the image memory 42, in which the pixels of the individual elemental images continue to be separately distinguishable. FIG. 6 depicts the organization of a preferred history buffer 130. The x,y coordinates of the history buffer 130 shown on the top surface 132 correspond to the maximum sight area of a displayed EFOV image. The column depth z of the history buffer is the maximum number of pixels of different elemental images which can be stored and combined to form each pixel of the EFOV image. In the illustrated embodiment the history buffer is shown to be six pixels deep as shown by delineations 132. In a constructed embodiment the history buffer may be eight to sixteen pixels deep.

Figure 5A:
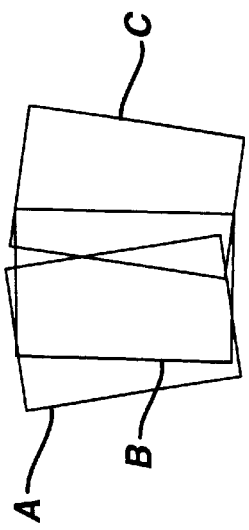
Figure 7A:
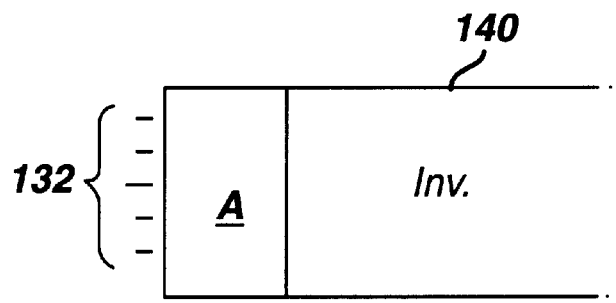
FIGS. 7a–7c illustrate how successive elemental images are entered into the history buffer of FIG. 6.
Figure 7B:
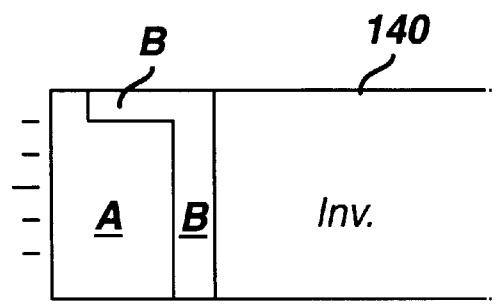
Figure 7C:
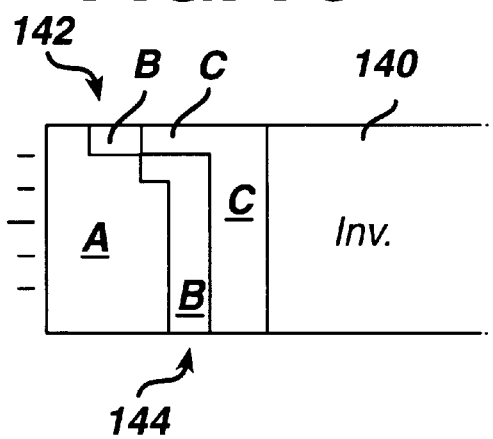

Referring to FIG. 5a, three exemplary elemental images A, B, and C are shown which are acquired as the initial elemental images for an EFOV image. Image A is the first to be acquired as the scanhead moves from left to right to acquire images A, B, and C in succession. Image A is therefore entered first into the history buffer 130 and is aligned to the left edge of the buffer as shown in FIG. 6. If the scanhead were moving from right to left, the first image A would be aligned at the right side of the buffer so that the EFOV image could be extended from right to left instead of from left to right as depicted in this example. When the image A is entered into the history buffer, it completely fills the pixel storage areas (depth z) beneath its x,y coordinates with image A pixel values as shown in FIG. 7a. FIGS. 7a–7c depict the history buffer cross-section in a plane 140 between arrows 7—7 in FIG. 6. The remaining pixel storage areas of the history buffer continue to be set to invalid values at this time.

Image B is next acquired and aligned with image A as described above. Image B is stored in the history buffer in its aligned position in x,y coordinates with respect to image A. Where image B overlays image A, the image A pixels are "pushed down" by one pixel depth so that the upper pixel is occupied by pixel B and the remaining are still occupied by image A pixel values, as shown in FIG. 7b. In areas where image B does not overlay image A, the full pixel depth is filled with image B pixel values.

When image C is acquired and aligned with image B the push down process is repeated as shown in FIG. 7c. In the columns indicated by arrow 142 where all three images overlap, the top pixel is from image C, the next pixel down is from pixel B, and the remaining pixel depth is filled with image A pixels. In image areas where only images B and C overlap, the top pixel in the column is an image C pixel, and those below are image B pixels.

This process continues as additional elemental images are acquired to extend the EFOV image. The finite depth of the history buffer, six pixels in this example, limits the number of images which can overlap at any pixel location to the most recent six overlapping images. Older image pixels at the location are "pushed out" of the bottom of the buffer which, in the z direction, operates as a FIFO (first in, first out) buffer. This is unlike the above-described technique of simply adding a new elemental image to an EFOV image, where an unlimited number of overlapping images are blended together. The finite limit of the history buffer provides a benefit of reduced image blurring as compared to the technique of simply recursively blending an EFOV image, since very old images in the history buffer overlay are removed by the FIFO push-down process. This is not possible where elemental images are blended into the EFOV image and are no longer separately distinguishable, unless each elemental image is stored and its position tracked for subsequent subtraction from the EFOV image. In addition the history buffer readily permits the scanning direction to be reversed during a scan. Another benefit is that the algorithm for combining elemental images into an EFOV image can be changed and different algorithms applied to the same extended image set.

Each time a new elemental image is added to the history buffer the combining algorithm is applied to the pixel data to form a pixel of an EFOV image from each column of pixels in the history buffer. It is seen that the initial filling of an entire column with pixels of the first image acquired at an x,y coordinate effects a weighting of the pixel data in favor of the initial image. If such weighting is not desired, the columns in the history buffer could only be filled one pixel depth at a time, or by another desired depth weighting. The combining algorithm may effect a summing of the pixel data at each column, an averaging or median filtering process, or some other linear or nonlinear filtering function (FIR, IIR, static, conditional, or adaptive) automatically or adaptively selected or chosen by the user. The EFOV image for elemental images A, B, and C would appear as shown by outline 120 in FIG. 5b.

Figure 8A:
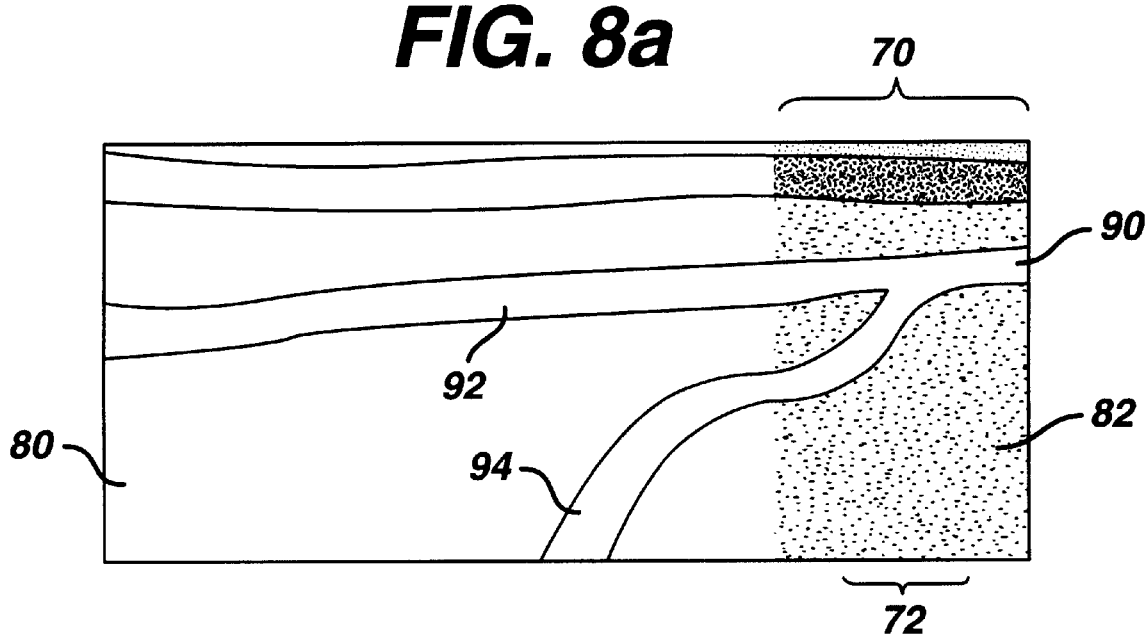
FIGS. 8a–8b illustrate the assembly of an extended field of view ultrasonic image from the central portions of successive elemental ultrasonic images.
Figure 8B:
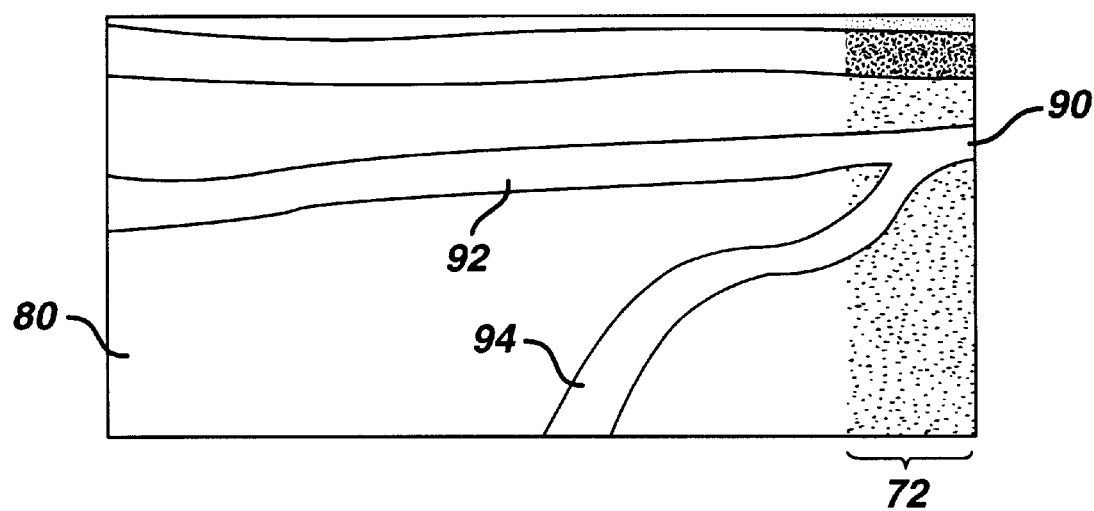

In accordance with a further aspect of the present invention, the full elemental image is not used in the EFOV image, but only the central portion of the elemental image, as shown in FIGS. 8a and 8b. FIG. 8a shows an EFOV image 80 which is extended by a new elemental image 82. The full new elemental image 82 is that obtained by the full aperture of the array transducer, as delineated by bracket 70 above the new image 82. However, only the central portion of the new image 82, the portion that is above bracket 72 and comprises only approximately 20% of the full image width, is added to the EFOV image 80. This percentage can be adjusted depending upon scanning parameters such as the image acquisition or display frame rate. The central portion of the new image 82 is formed by the center of the array aperture, where the image is generally in its best focus. The central portion is formed by a balanced aperture, is (in the case of a phased array) steered directly ahead, and will most likely result from the best acoustic coupling to the body. Accordingly, since the central portion of the image is likely to be the most highly resolved image area, only the central area of the new elemental image is combined with the previously formed EFOV image. The resultant EFOV image with the addition of this central image area of elemental image 82 is illustrated in FIG. 8b.

In addition to producing grayscale B mode images, most ultrasound systems produce images in which the motion or flow of tissue and fluids is depicted in color. Colorflow (velocity) imaging, Doppler power imaging, power motion imaging, and tissue Doppler imaging are modes in which motion and flow are imaged, either alone or in combination with B mode structural image data. In accordance with a further aspect of the present invention, two extended image memories 42 are used for EFOV images in these compound modes. Preferably two history buffers 130 are used, one in which the B mode image information is registered and stored, and a second in which the corresponding flow or motion image information is registered and stored. The use of two buffers allows flexibility in using different techniques for combining the elemental images of the two buffers into one EFOV image. In one approach, the combining algorithm first produces a B mode EFOV image from the data of one history buffer and a color EFOV image from the data of the other history buffer. These EFOV images can be alternately displayed or displayed simultaneously in different areas of the viewing screen. Alternatively, elemental images from the two buffers can be combined directly into an EFOV image based upon the distribution of the image data. For a composite EFOV image the combining algorithm combines the B mode and color data into a single EFOV image. The data of the two buffers is combined by preferentially using B mode data where data of both types is available at one EFOV pixel, by preferentially using color data when the color data exceed a predetermined threshold, or by blending the two together to form a pixel with a hue or color determined by characteristics of both data types.

What is claimed is:

1. A method for spatially aligning two ultrasonic images for display in an extended field of view image comprising the steps of:

receiving ultrasonic images of a high resolution;

processing the image data of said ultrasonic images to produce image data of different resolution levels for each ultrasonic image;

comparing corresponding resolution level image data of said ultrasonic images;

aligning lower resolution ultrasonic images on the basis of the result of said comparing step;

aligning higher resolution images which have been previously aligned at a lower resolution; and combining aligned high resolution images to form an extended field of view image.

2. The method of claim 1, wherein said step of processing comprises producing image data of a lower resolution level by one or more of the steps of filtering, subsampling, truncating, or decimating.

3. The method of claim 1, wherein said step of comparing comprises comparing lower resolution level data of said two images, pre-aligning said ultrasonic images on the basis of the results of comparing lower resolution level data, and comparing higher resolution level data of said two images which have been pre-aligned.

4. A method for spatially aligning two medical ultrasonic diagnostic images for display in an extended field of view image comprising the steps of:

identifying feature areas of one of said images which contain prominent image features;

comparing the feature areas of said one of said images with corresponding areas of the other of said images to ascertain the spatial displacement between said images; and aligning said ultrasonic images on the basis of said spatial displacement, further comprising the step of processing the image data of said ultrasonic images to produce image data of different resolution levels for each ultrasonic image;

wherein said step of identifying feature areas identifies different numbers of feature areas for image data of different resolution.

5. The method of claim 4, wherein fewer feature areas are identified for image data of lower resolution than are identified for image data of higher resolution.

6. A method for spatially aligning two ultrasonic images comprising the steps of:

performing a SAD analysis of pixel areas of said two images to determine a minimum SAD value;

refining parameters of said minimum SAD value; and aligning said ultrasonic images on the basis of refined parameters of said minimum SAD value, wherein said step of refining comprises a gradient search for a better minimum SAD value by offsetting one or more displacement parameters.

7. The method of claim 6, wherein said step of refining comprises eliminating boundary condition results.

* * * * *